(12) United States Patent
Muto et al.

(10) Patent No.: US 9,468,503 B2
(45) Date of Patent: Oct. 18, 2016

(54) DRIVE MOTOR OF DENTAL HANDPIECE

(71) Applicant: NAKANISHI INC., Tochigi (JP)

(72) Inventors: Shinichiro Muto, Tochigi (JP); Hayato Matsushita, Tochigi (JP); Akito Nakamura, Tochigi (JP)

(73) Assignee: NAKANISHI INC., Tochigi (JP)

( * ) Notice: Subject to any disclaimer, the term of this patent is extended or adjusted under 35 U.S.C. 154(b) by 253 days.

(21) Appl. No.: 14/032,583

(22) Filed: Sep. 20, 2013

(65) Prior Publication Data

US 2014/0087329 A1   Mar. 27, 2014

(30) Foreign Application Priority Data

Sep. 24, 2012   (JP) ................. 2012-209323

(51) Int. Cl.
| | |
|---|---|
| A61C 1/06 | (2006.01) |
| H02K 9/02 | (2006.01) |
| H02K 9/16 | (2006.01) |
| A61C 1/05 | (2006.01) |

(52) U.S. Cl.
CPC ............... *A61C 1/055* (2013.01); *A61C 1/06* (2013.01); *H02K 9/02* (2013.01); *H02K 9/16* (2013.01)

(58) Field of Classification Search
CPC ............ H02K 9/00; H02K 9/02; H02K 9/08; H02K 9/10; H02K 9/14; H02K 9/16; A61C 1/055; A61C 1/06
USPC ....... 310/50, 52, 58, 59, 60 A; 433/103, 104, 433/114, 115, 131, 132
See application file for complete search history.

(56) References Cited

U.S. PATENT DOCUMENTS

| | | | |
|---|---|---|---|
| 3,487,546 A * | 1/1970 | Fleer | A61C 1/06 433/104 |
| 4,007,529 A | 2/1977 | Fleer | |
| 4,237,393 A * | 12/1980 | Landgraf | A61C 1/052 310/154.18 |
| 6,425,761 B1 * | 7/2002 | Eibofner | 433/131 |
| 8,333,588 B2 * | 12/2012 | Putz et al. | 433/131 |
| 2003/0165794 A1 | 9/2003 | Matoba | |
| 2008/0150375 A1 * | 6/2008 | Shima | 310/50 |
| 2009/0160269 A1 | 6/2009 | Bischof et al. | |
| 2010/0270877 A1 * | 10/2010 | Esenwein et al. | 310/62 |

FOREIGN PATENT DOCUMENTS

| | | |
|---|---|---|
| DE | 10033577 A1 | 4/2001 |
| JP | S45-33959 | 10/1970 |
| JP | S52-118894 A | 10/1977 |
| JP | S54-150892 A | 11/1979 |
| JP | 2001-029361 A | 2/2001 |
| JP | 2001-086721 A | 3/2001 |
| JP | 2001086721 A * | 3/2001 |
| JP | 2005-342403 A | 12/2005 |
| JP | 2007-267913 A | 10/2007 |

* cited by examiner

*Primary Examiner* — Quyen Leung
*Assistant Examiner* — Minki Chang
(74) *Attorney, Agent, or Firm* — Pearne & Gordon LLP

(57) ABSTRACT

A drive motor of a dental handpiece for driving a cutting tool of the handpiece is provided that is connected to the dental handpiece on its front end side and includes a cylindrical casing; a rotor unit, which is rotatably supported inside the casing and outputs a driving force; a stator unit provided around the rotor unit inside the casing; and an air path which causes cooling air supplied from the rear end side of the drive motor to pass through an airtight cooling room circumferentially extending between the stator unit and the casing, and to be discharged from the rear end side.

7 Claims, 10 Drawing Sheets

DRIVE MOTOR OF DENTAL HANDPIECE

BACKGROUND

1. Technical Field

The present invention relates to a drive motor for driving a cutting tool of a dental handpiece, more particularly to a cooling structure of the motor.

2. Related Art

Motor-driven type dental handpieces include a tooth cutting handpiece, a surgical (or implant) handpiece and a root canal treatment handpiece, and the like. The tooth cutting handpiece is used for cutting a tooth, the surgical handpiece is used for drilling a hole into a jawbone and for fixing an implant in a dental implant operation, and the root canal treatment handpiece is used for cutting or enlarging a root canal.

In the motor-driven type dental handpiece, as illustrated in FIG. 9, a handpiece 200 includes a first rotation shaft 202, which rotates in engagement with a drive shaft inside the top end connecting part 201 of an electric motor M; a second rotation shaft 203, which is tilted with respect to the first rotation shaft 202; a first gear train 204, which links the first rotation shaft 202 and the second rotation shaft 203; a tool rotating shaft 205 orthogonal to the second rotation shaft 203; and a second gear train 206, which links the second rotation shaft 203 and the tool rotating shaft 205. The first and second rotation shafts 202, 203, the first gear train 204, the tool rotating shaft 205, and the second gear train 206 construct a rotation transmitting mechanism as with, for example, JP 2005-342403 A.

The method for cooling a motor of each of these motor-driven type dental handpieces is different from the others depending on the type of the handpiece. The tooth cutting handpiece comprises a feeding path, through which air for cooling components of the handpiece including the motor (hereinafter, called as "cooling air") is fed for suppressing heat generation due to high speed rotation of the cutting tool. The cooling air fed through a connection hose passes through the inside of both the motor and the handpiece, and is discharged outside from the top end of the handpiece where the cutting tool is mounted as with, for example, JP 2005-342403 A and 2001-29361 A.

On the other hand, in the case of the surgical handpiece and the root canal treatment handpiece, cooling air is not used for the sake of avoiding unwanted bacteria included in the cooling air to be fed to the affected area, and the motor is upsized for securing its thermal capacity or the motor is cooled by use of a fan as with, for example, JP 2007-267913 A.

SUMMARY

For the reason described above, there has been a problem such that the motor of a conventional surgical handpiece is difficult for an operator to handle since being bigger and heavier as compared with the motor of a tooth cutting handpiece. The present invention addresses the above problem with the object of downsizing the motor used for a surgical handpiece.

In order to achieve the above object, a drive motor of a dental handpiece of the present invention includes a cylindrical casing; a rotor, which is rotatably supported inside the casing and outputs a driving force; a stator provided around the rotor inside the casing; and a first air path, which causes cooling air supplied from the rear end side to pass through an airtight cooling room circumferentially extending between the stator and the casing, and to be discharged from the rear end side. According to such a configuration, since the cooling air supplied from the rear end side passes through the airtight cooling room circumferentially extending between the stator and the casing, and is discharged from an air-discharging pipe on the rear end side by providing the first air path, it is possible to cool the motor without causing the cooling air to be discharged toward the surgical handpiece.

It is preferable that the motor of the present invention includes a second air path, which causes cooling air supplied from the rear end side to pass through an airtight cooling room and to be discharged from the front end side, in addition to the first air path. According to such a configuration, in the case of connecting a tooth cutting handpiece, since it is possible to cool a rotation transmitting mechanism through the second air path at the same time as cooling the motor through the first air path, the motor of the present invention can be used for both the tooth cutting handpiece and the surgical handpiece. That is, if it is assumed that a first handpiece not having a channel for feeding cooling air and a second handpiece having a channel for feeding cooling air are selectively connected to the motor of the present invention on its front end side, the cooling air is supplied only to the first air path when the first handpiece is connected, while the cooling air is supplied to both the first and second air paths when the second handpiece is connected. Here, the first handpiece not having a channel for feeding cooling air at least includes a surgical handpiece and a root canal treatment handpiece.

The stator of the motor of the present invention may include a stator body including an electromagnetic coil and a magnetic core, and a sleeve holding the stator body. Thereby the airtight cooling room is preferably partitioned by the sleeve in the radial direction of the casing. There is an advantage that the airtight room can be easily formed by utilizing the sleeve holding the stator body.

As described above, according to the present invention, since having the first air path that causes cooling air supplied from the rear end side to pass through the airtight cooling room circumferentially extending between the stator and the casing, and to be discharged from the rear end side, even when a surgical handpiece is connected to the front end side, the motor can be cooled while the cooling air is avoided from being discharged toward the surgical handpiece. It is therefore possible to provide a small-size motor with respect to the surgical handpiece according to the present invention. Additionally, according to the present invention with the second air path that causes cooling air supplied from the rear end side to pass through an airtight cooling room and to be discharged from the front end side in addition to the first air path, a motor used for both a tooth cutting handpiece and the surgical handpiece is provided.

BRIEF DESCRIPTION OF DRAWINGS

FIG. 2A is a side view thereof and FIG. 2B is a rear view thereof;

FIG. 3A is a view along arrows IIIa-IIIa, FIG. 3B is a view along arrows IIIb-IIIb, and FIG. 3C is a view along arrows IIIc-IIIc;

DETAILED DESCRIPTION

Figure 1:
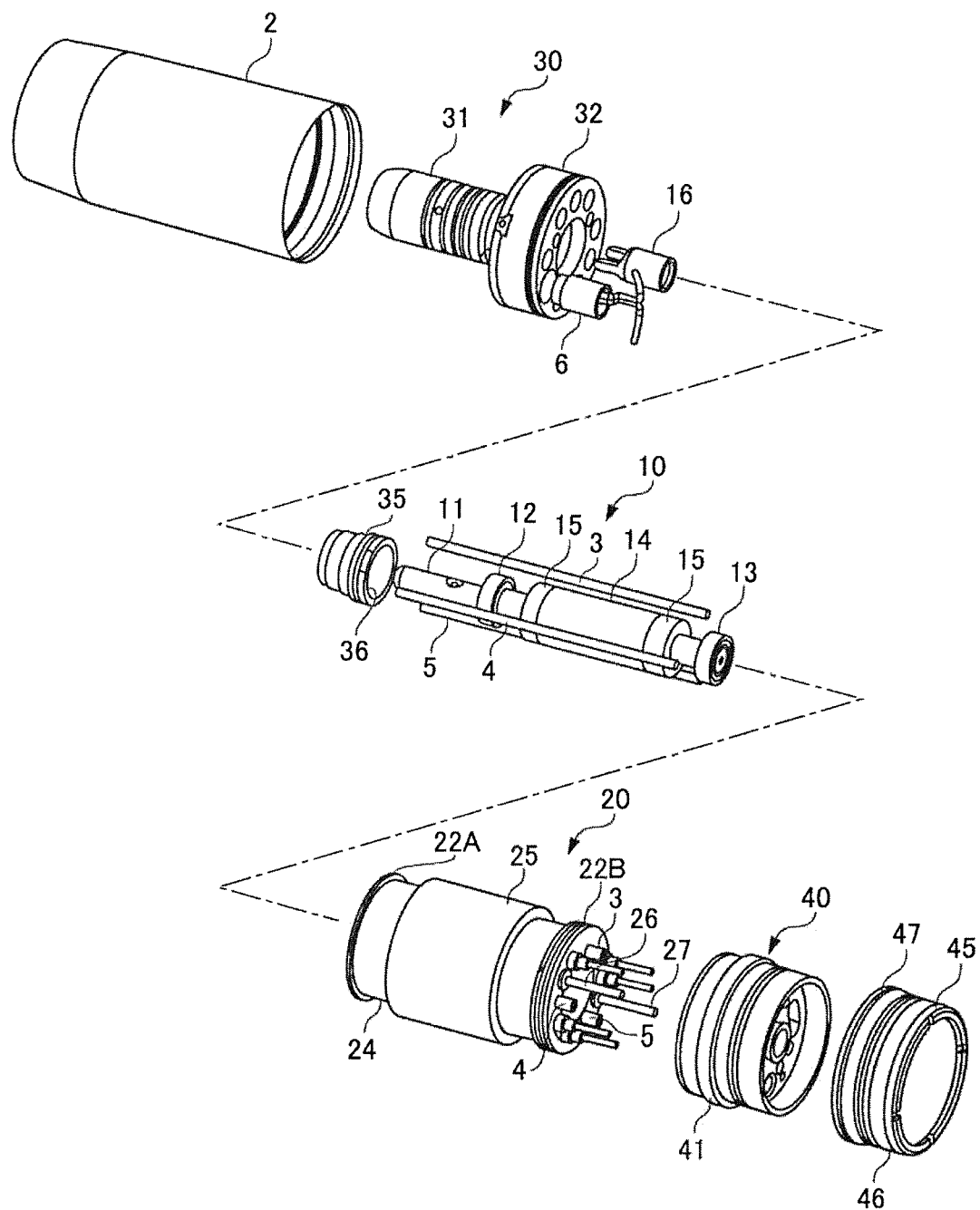
FIG. 1 is an exploded perspective view of a motor of the present embodiment.
Figure 2B:
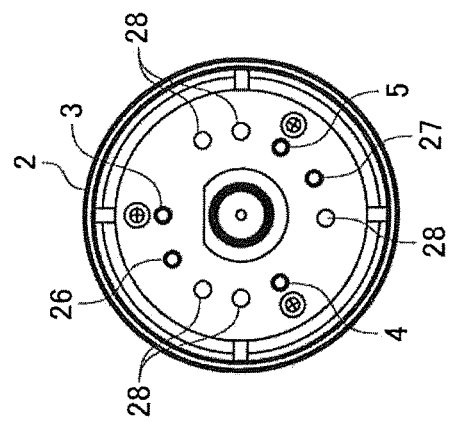
FIGS. 2A and 2B show the motor presented in FIG. 1.
Figure 2A:
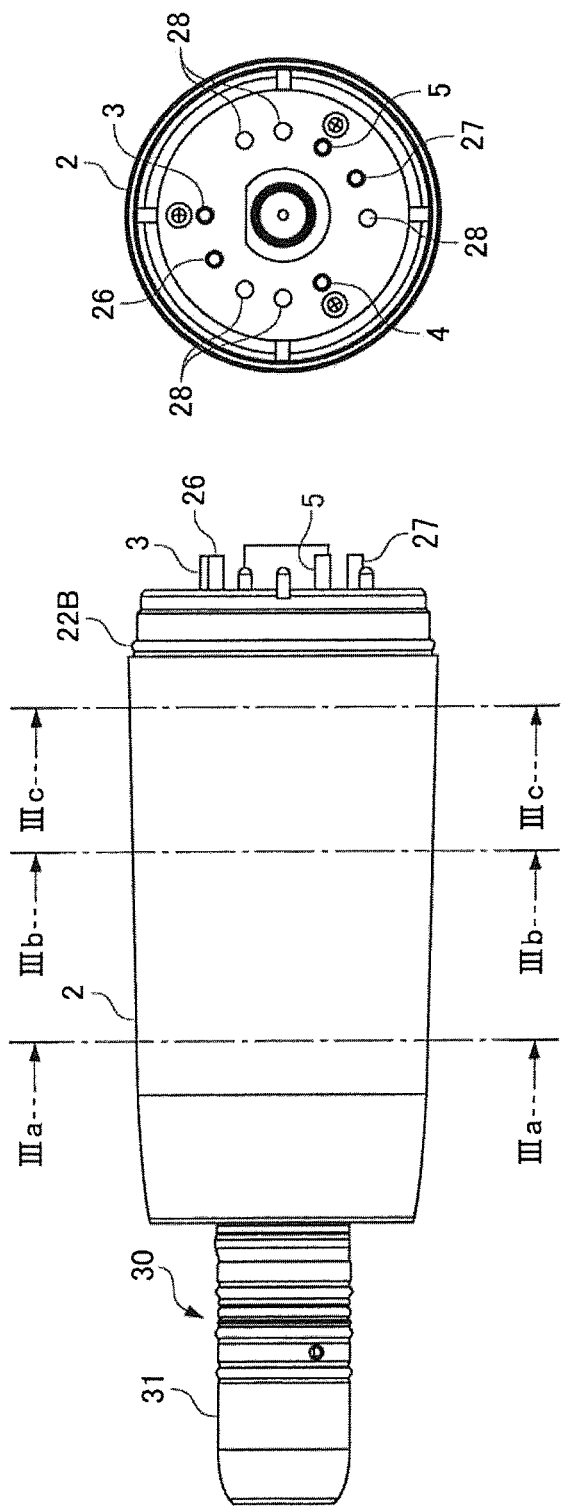
Figure 3A:
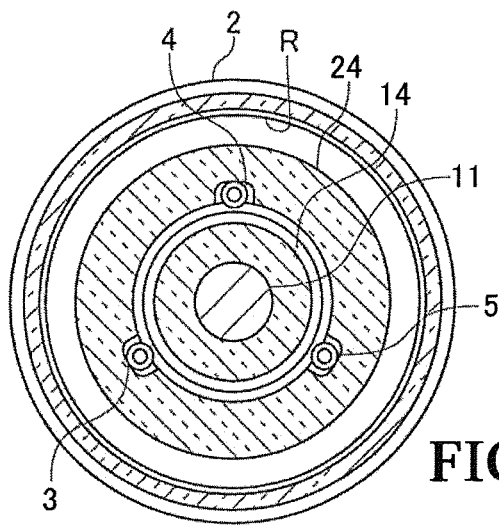
FIGS. 3A to 3C are cross-sectional views of the motor presented in FIGS. 2A and 2B.
Figure 3B:
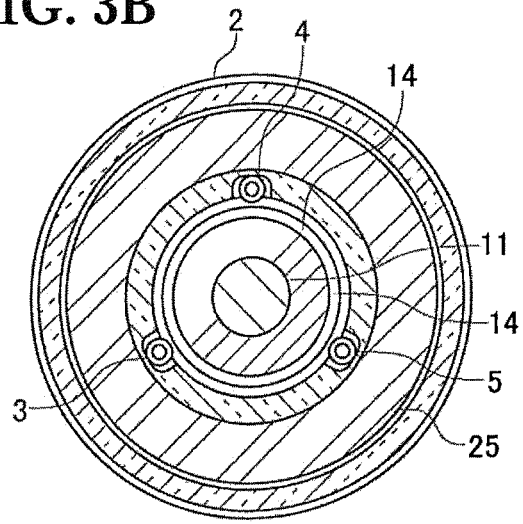
Figure 3C:
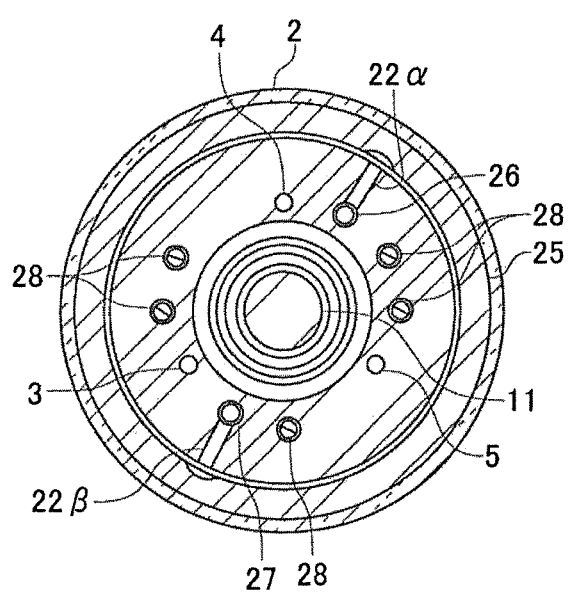
Figure 4A:
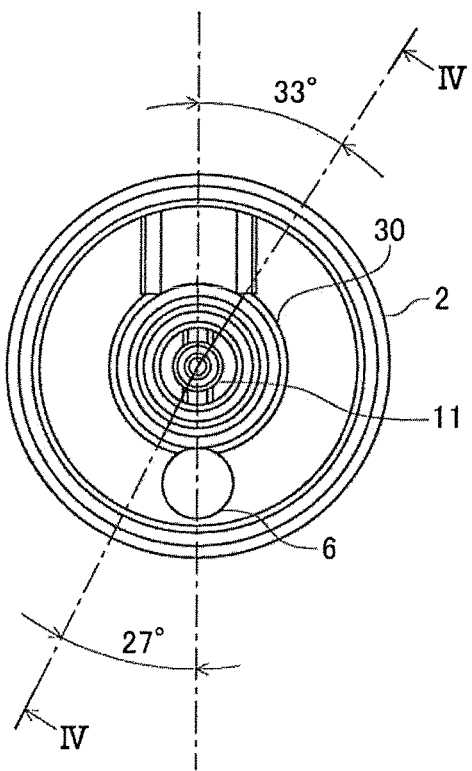
FIG. 4A is a cross-sectional elevation view of the motor presented in FIG. 5.
Figure 4B:
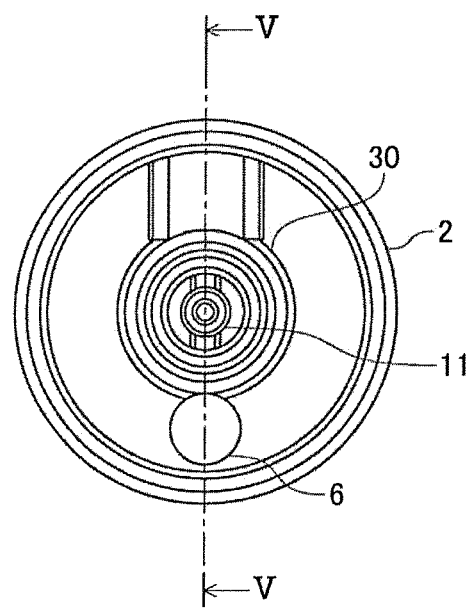
FIG. 4B is a cross-sectional elevation view of the motor presented in FIG. 6.
Figure 5:
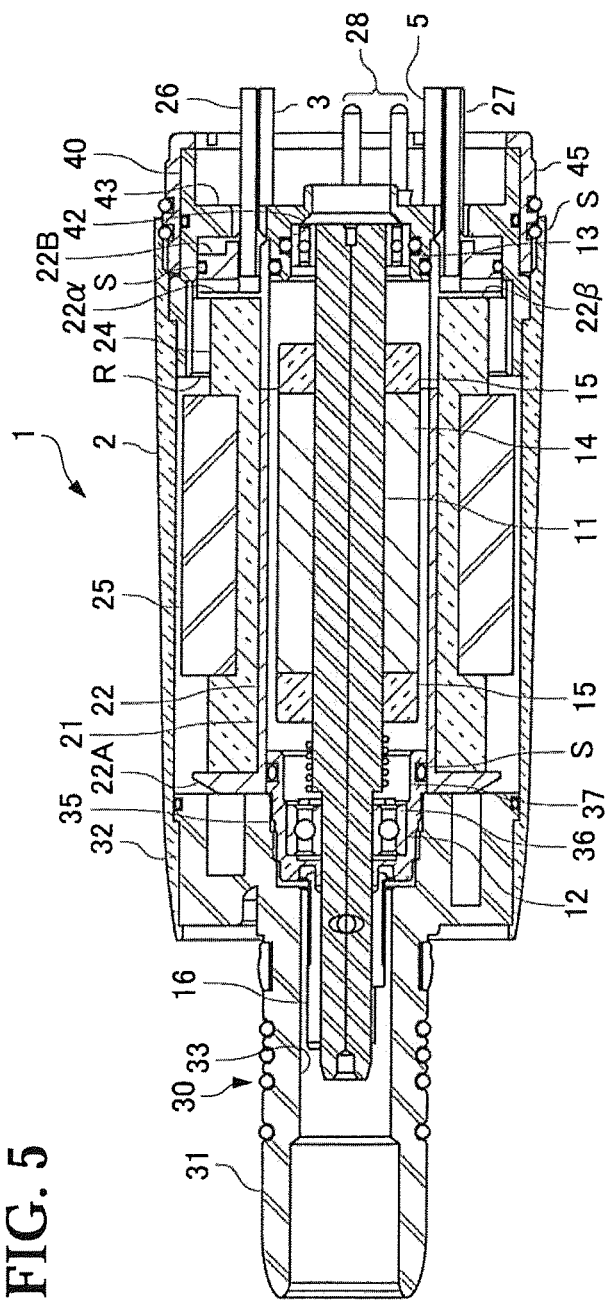
FIG. 5 is a cross-sectional view of the motor presented in FIG. 4A along arrows IV-IV.
Figure 6:
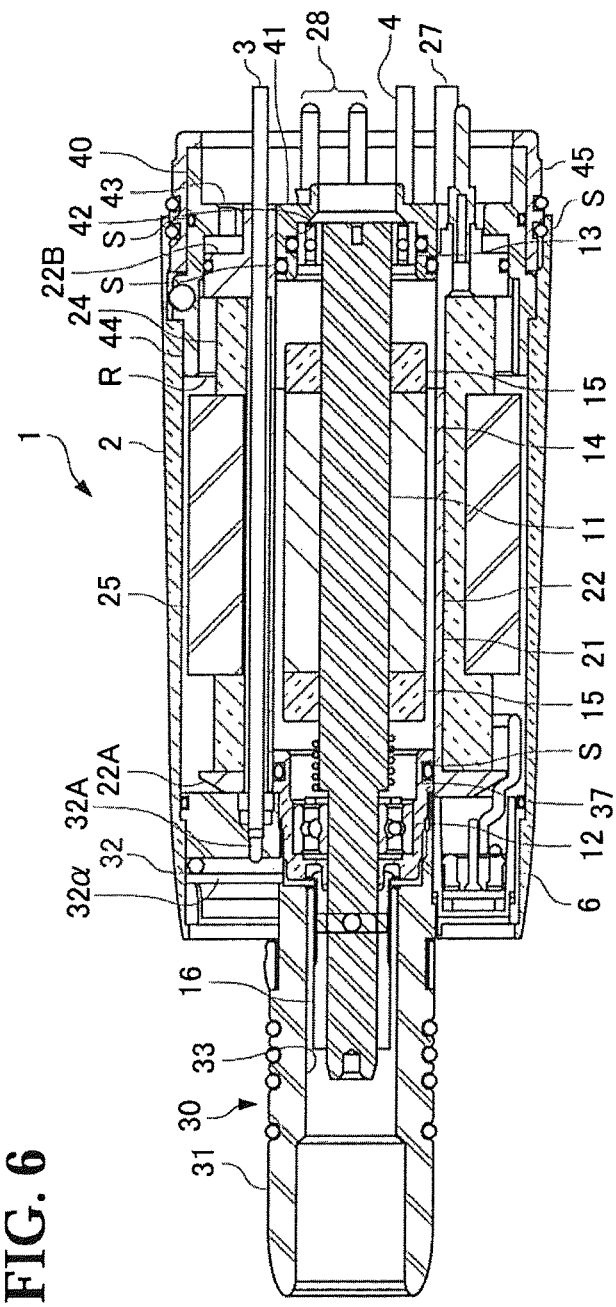
FIG. 6 is a cross-sectional view of the motor presented in FIG. 4B along arrows V-V.

The present invention will be described in detail below on the basis of the embodiment illustrated in FIGS. 1 to 6. The present embodiment exemplifies a motor 1 used for both a tooth cutting handpiece and a surgical handpiece. As illustrated in FIG. 1, the motor 1 comprises a rotor unit 10 and a stator unit 20 as main components concerned with driving thereof. The rotor unit 10 and the stator unit 20 are housed coaxially in the inside of a hollow cylindrical casing 2, and are installed inside the casing 2 by being fixed by an insertion cylinder 30 on its one end and by being fixed by a rear holder 40 (fixing ring 45) on its other end. The motor 1 provides a rotational driving force to a cutting tool by being connected to the rotation transmitting mechanism (not illustrated) of the handpiece in a housing cavity 33 of the insertion cylinder 30. The specific configuration of each of the components will be described below in turn. It is noted that the following description proceeds on the basis of definition that the side connected to the rotation transmitting mechanism is denoted as the front and the other side is denoted as the rear.

[Rotor Unit 10]

The rotor unit 10 generates the rotational driving force by being acted upon by the magnetic field due to the stator unit 20. The rotor unit 10 comprises a drive shaft 11, which outputs the rotational driving force toward the rotation transmitting mechanism of the handpiece; a front bearing 12, which supports the drive shaft 11 on the front side; and a rear bearing 13, which supports the drive shaft 11 on the rear end, and thereby the drive shaft 11 is rotatably supported in the casing 2. The front bearing 12 and the rear bearing 13 each are a radial bearing having spherical rolling elements between the inner and outer races. On the outer periphery of the drive shaft 11, a cylindrical permanent magnet 14 is fitted between the front bearing 12 and the rear bearing 13. The permanent magnet 14 is robustly fixed to the drive shaft 11 so as not to be displaced both axially and circumferentially by having fixing rings 15, 15 on the front and rear ends, respectively. The front side of the drive shaft 11 with respect to the front bearing 12 is disposed in the inside of the housing cavity 33 of the insertion cylinder 30 and is connected to the rotation transmitting mechanism (not illustrated). For the purpose of this connection, a claw clutch 16 is mounted on the front end side of the drive shaft 11. Although the rotor unit 10 includes the drive shaft 11 having the permanent magnet 14 disposed therearound, it is noted that the present invention is not limited to this application and may be widely applied to a rotor which is rotationally driven by being subjected to a magnetic field generated from the stator unit 20. The material of each of the drive shaft 11 and permanent magnet 14 is not restricted, and it is possible to use an anticorrosive metal such as, for example, stainless steel, titanium alloy, or the like as the material of the drive shaft 11, and to use a rare-earth permanent magnet such as, for example, Ne—Fe—B magnet or the like having high magnetic characteristics as the permanent magnet 14. Likewise, the material of the casing 2 and other components including ones described below is able to be appropriately chosen on the basis of required characteristics.

[Stator Unit 20]

The stator unit 20 generates a magnetic field toward the rotor unit 10, specifically toward the permanent magnet 14 by being energized. The stator unit 20 comprises a partition sleeve 21, an electromagnetic coil 24 held by the partition sleeve 21, and a stator core 25 held on the outer periphery of the electromagnetic coil 24.

The partition sleeve 21 comprises a cylindrical sleeve body 22, a front flange 22A disposed at the front end of the sleeve body 22, and a rear flange 22B disposed at the rear end of the sleeve body 22, and the electromagnetic coil 24 and the stator core 25 are placed therebetween. The front flange 22A and rear flange 22B each extend radially outward of the sleeve body 22.

The stator unit 20 is arranged around the rotor unit 10 with a predetermined spacing, and is housed inside the casing 2 so as to have a predetermined circumferential spacing between the outer periphery of the stator core 25 and the inner periphery of the casing 2.

In the rear flange 22B, there are formed an air-feeding passage 22α and an air-discharging passage 22β, each of which is formed from its outer periphery to a predetermined depth and has a circular opening. The air-feeding passage 22α and the air-discharging passage 22β are formed at substantially symmetrical positions. An air-feeding pipe 26 and an air-discharging pipe 27 are supported at the rear flange 22B; the air-feeding pipe 26 is passed through from the rear end face of the rear flange 22B to the air-feeding passage 22α, and the air-discharging pipe 27 is passed through from the rear end face of the rear flange 22B to the air-discharging passage 22β. Although described in detail later, cooling air supplied from an air supply source passes through the air-feeding pipe 26 and air-feeding passage 22α and is fed to a cooling room R (refer to FIGS. 7, 8A, and 8B) between the casing 2 and the stator unit 20. Since the cooling air is continuously fed to the cooling room R, a surplus amount thereof passes through the air-discharging passage 22β and the air-discharging pipe 27, and is discharged to the outside of the motor 1.

Incidentally, although provided with one each in the above description, the air-feeding pipe 26 and the air-discharging pipe 27 may be each provided in a plural number. In this case, it is possible to form the air-feeding passage 22α and the air-discharging passage 22β so as to fit thereto.

[Insertion Cylinder 30]

The insertion cylinder 30 is fixed to the enclosure (not illustrated) of a handpiece on its front end side and seals the front end side of the motor 1 on its rear end side.

The insertion cylinder 30 consists of a small-diametered connecting section 31 and a large-diametered sealing section 32 lying in line with the connecting section 31. The insertion cylinder 30 is placed in the motor 1 so that the connecting section 31 is positioned on its front end side and the sealing section 32 is positioned on its rear end side. In the insertion cylinder 30, there is formed the housing cavity 33 that passes axially through the connecting section 31 and the sealing section 32.

The housing cavity 33 is configured such that its rear end side has a larger diameter as compared to its front end side, and a hollow, cylindrical front holder 35 is mounted on the rear end side. The front holder 35 comprises a holding cavity 36 for housing and holding the front bearing 12. By being fixed to holding cavity 36, the front bearing 12 is secured in the insertion cylinder 30 through the front holder 35. On the rear end side of the front holder 35, there is formed a support part 37 that extends rearward further than the rear end face of the sealing section 32. The support part 37 supports the partition sleeve 21 on the front end side of the partition sleeve 21 by being fitted inside the partition sleeve 21 of the above-mentioned stator unit 20. The partition sleeve 21 is disposed so that the front end face thereof is in contact to the rear end face of the sealing section 32. The drive shaft 11 passes through the sealing section 32, and the front end side thereof extends up to the vicinity of the midpoint of the housing cavity 33 of the connecting section 31. The drive shaft 11 is connected to the rotation transmitting mechanism in the inside of the connecting section 31.

Hermetical sealing between the insertion cylinder 30 and casing 2 is achieved by that the sealing section 32 is fitted into the inside of the casing 2 through a seal ring S. In addition, the insertion cylinder 30 hermetically seals between the inside and outside of the stator unit 20 by that the support part 37 is fitted into the inside of the partition sleeve 21 through another seal ring S.

[Cooling Air Pipe 3]

The motor 1 comprises a cooling air pipe 3. The cooling air pipe 3 serves to convey cooling air, which is supplied from an air supply source, to the sealing section 32 of the insertion cylinder 30 without leaking it on its way. The front end side of the cooling air pipe 3 is inserted into a holding hole 32A, which is formed in the sealing section 32 up to a predetermined depth along the axial direction, and the rear end side of the cooling air pipe 3 is passed through the rear flange 22B of the partition sleeve 21 and also a flange 43 of the rear holder 40 to be led out to the outside of the motor 1. The top end of the holding hole 32A communicates with an air-feeding passage 32α formed along a radial direction in the sealing section 32. The air-feeding passage 32α communicates with the housing cavity 33 on its inner side in the radial direction, but is sealed on its outer side in the radial direction. The cooling air fed from the rear end side of the cooling air pipe 3 passes through the stator unit 20 and sealing section 32, and is discharged into the housing cavity 33. The cooling air cools the rotation transmitting mechanism by flowing axially forward in the periphery of the rear holder 40 and then flowing axially forward between the drive shaft 11 and connecting section 31 of the insertion cylinder 30.

[Rear Holder 40]

The rear holder 40 houses and holds the rear bearing 13, which supports the drive shaft 11 on the rear end of the rotor unit 10. The rear holder 40 includes a holder body 41, which comprises a housing cavity 42 housing the rear bearing 13; a flange 43 extending from the rear end side of the holder body 41 inwardly in its radial direction; a fitting wall 44, which lies in line with the top end of the flange 43 and extends in the axial direction; and a fixing ring 45 for securing the rear holder 40 to the casing 2. The holder body 41 supports the rear end side of the partition sleeve 21 by being fitted inside the partition sleeve 21 of the stator unit 20. The rear holder 40 is held inside the casing 2 by that the fitting wall 44 is fitted inside the casing 2, and the rear bearing 13 is thereby held in the casing 2 through the rear holder 40. The rear holder 40 is fixed to the casing 2 by means of the fixing ring 45. The fixing ring 45 comprises a hollow ring body 46 and male threads 47 formed on the outer peripheral surface of the ring body 46. The rear holder 40 is fixed to the casing 2 by that the male threads 47 are screwed in female threads (not illustrated) formed on the inner peripheral surface of the casing 2.

Hermetical sealing between the rear holder 40 and the casing 2 is achieved by that the fixing ring 45 (ring body 46) is fitted inside the casing 2 through a seal ring S, and another seal ring S is involved between the fixing ring 45 and fitting wall 44. In addition, the rear holder 40 hermetically seals between the inside and outside of the stator unit 20 by that the holder body 41 is fitted into the inside of the partition sleeve 21 through a seal ring S. Moreover, a seal ring S is involved between the fitting wall 44 and the rear flange 22B of the stator unit 20. On the rear end side of the motor 1, hermetical sealing between the casing 2 and stator unit 20 is thus achieved.

[Other Components]

The motor 1 comprises a chip air pipe 4 and a water-feeding pipe 5. The chip air pipe 4 feeds air, which is supplied from an outside supply source, toward the top end (cutting tool) of the handpiece, and the water-feeding pipe 5 feeds water, which is supplied from an outside supply source, toward the top end (cutting tool) of the handpiece. These air and water are used in an oral cavity. The motor 1 also comprises an LED light source 6. The LED light source 6 is installed for lighting a treatment area during treatment with the handpiece, and the electric power for the motor 1 and the LED light source 6 is supplied through electrodes 28. Since the structure and effect of each of the above components are well known to those skilled in the art as described in, for example, JP 2005-342403 A and 2001-29361 A, further specific descriptions are omitted.

The motor 1 according to the present embodiment comprises a first path and a second path as the path for feeding cooling air. As specifically described later, the first path serves for feeding the cooling air in either case in which the motor 1 is used for a tooth cutting handpiece and a surgical handpiece, while the second path serves for feeding the cooling air only in the case in which the motor 1 is used for a tooth cutting handpiece. The first and second paths are independent of each other.

[First Path]

The motor 1 is hermetically sealed between the casing 2 and the stator unit 20 on both its front end and rear end sides. That is, an airtight cooling room R is formed in between the casing 2 and the stator unit 20. When cooling air is fed to the air-feeding pipe 26, the cooling air passes the air-feeding passage 22α and flows in the cooling room R including a narrow space between the casing 2 and the stator unit 20. Since this narrow space extends in a circumferential direction, the cooling air serves for cooling the motor 1 by spreading around the stator unit 20 without being leaked. When the cooling air is continuously fed to the cooling room R, the surplus cooling air with respect to the cooling room R passes through the air-discharging passage 22β and is discharged from the air-discharging pipe 27 to the outside. The cooling air for cooling the motor 1 is thus discharged to the outside without flowing toward the handpiece. That is, the first path is provided for the reason that the cooling air cools the motor 1 by circulating or going around in the cooling room R.

[Second Path]

When cooling air is supplied to the cooling air pipe 3, the cooling air passes therethrough without leaking to the stator unit 20, and then flows into the inside of the housing cavity 33 through the air-feeding passage 32α formed in the sealing section 32. Further, the cooling air flows forward in the periphery of the front holder 35, and then flows forward in the housing cavity 33 of the insertion cylinder 30, by which the rotation transmitting mechanism is cooled. The second path thus serves to cool the rotation transmitting mechanism by causing the supplied cooling air to flow directly toward the housing cavity 33.

[Dental Treatment System]

Figure 7:
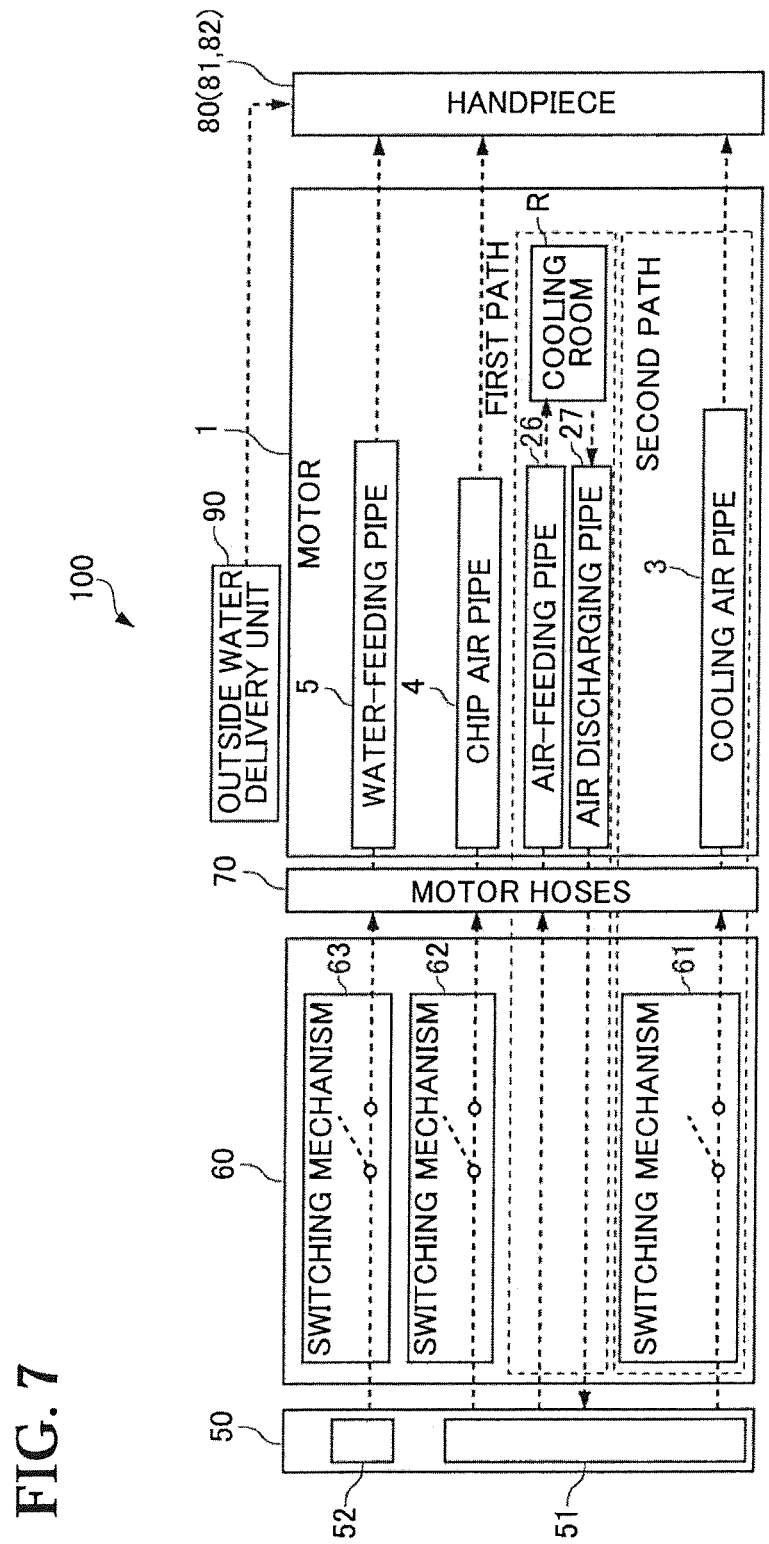
FIG. 7 is a block diagram showing the configuration of a dental treatment unit using the motor of the present embodiment.

A configuration example of a dental treatment system 100 provided with a handpiece, in which the motor 1 described above is incorporated, will be explained with reference to FIG. 7. The dental treatment system 100 comprises a dental unit 50; a controller 60 for controlling whether or not to feed cooling air and water from the dental unit 50; motor hoses 70 for feeding the cooling air and water fed from the dental unit 50 toward the motor 1; the motor 1; the handpiece 80 driven by the motor 1; and an outside water delivery unit 90.

The dental unit 50 comprises an air supply source 51 including, for example, a compressor, and a water supply source 52 including, for example, a pump. The controller 60 comprises three switching mechanisms 61, 62, 63. The switching mechanism 61 selectively switches whether or not (ON, OFF) to feed the cooling air toward the cooling air pipe 3, i.e., the second path. The switching mechanism 62 selectively switches whether or not (ON, OFF) to feed the cooling air toward the chip air pipe 4. The switching mechanism 63 selectively switches whether or not (ON, OFF) to feed the water toward the water-feeding pipe 5.

The motor hoses 70 include an air hose for feeding the cooling air, which is supplied through the switching mechanism 61, toward the cooling air pipe 3 of the motor 1; another air hose for feeding the cooling air, which is supplied through the switching mechanism 62, toward the chip air pipe 4 of the motor 1; and a water hose for feeding the water, which is supplied through the switching mechanism 63, toward the motor 1. The motor hoses 70 also include an air hose for feeding the cooling air, which is supplied from the dental unit 50, toward the air-feeding pipe 26, and another air hose for returning the cooling air discharged from the air-discharging pipe 27 to the dental unit 50.

A surgical handpiece 81 and a tooth cutting handpiece 82 are alternatively used as the handpiece 80. When collectively called, the both are denoted as the handpiece 80. It is noted that the motor 1 is used for both the surgical handpiece 81 and the tooth cutting handpiece 82. The outside water delivery unit 90 stores, for example, purified water to be supplied to the handpiece 80 when a surgical handpiece 81 is adopted as the handpiece 80, and comprises a pump for pressure-feeding the purified water toward the handpiece 80 and a hose for feeding the purified water. In the case of performing an implant operation by use of the surgical handpiece 81, it is required to feed not city water but, for example, purified water, in which proliferation of unwanted bacteria is restrained, to the affected area, so the outside water delivery unit 90 is provided.

Figure 8A:
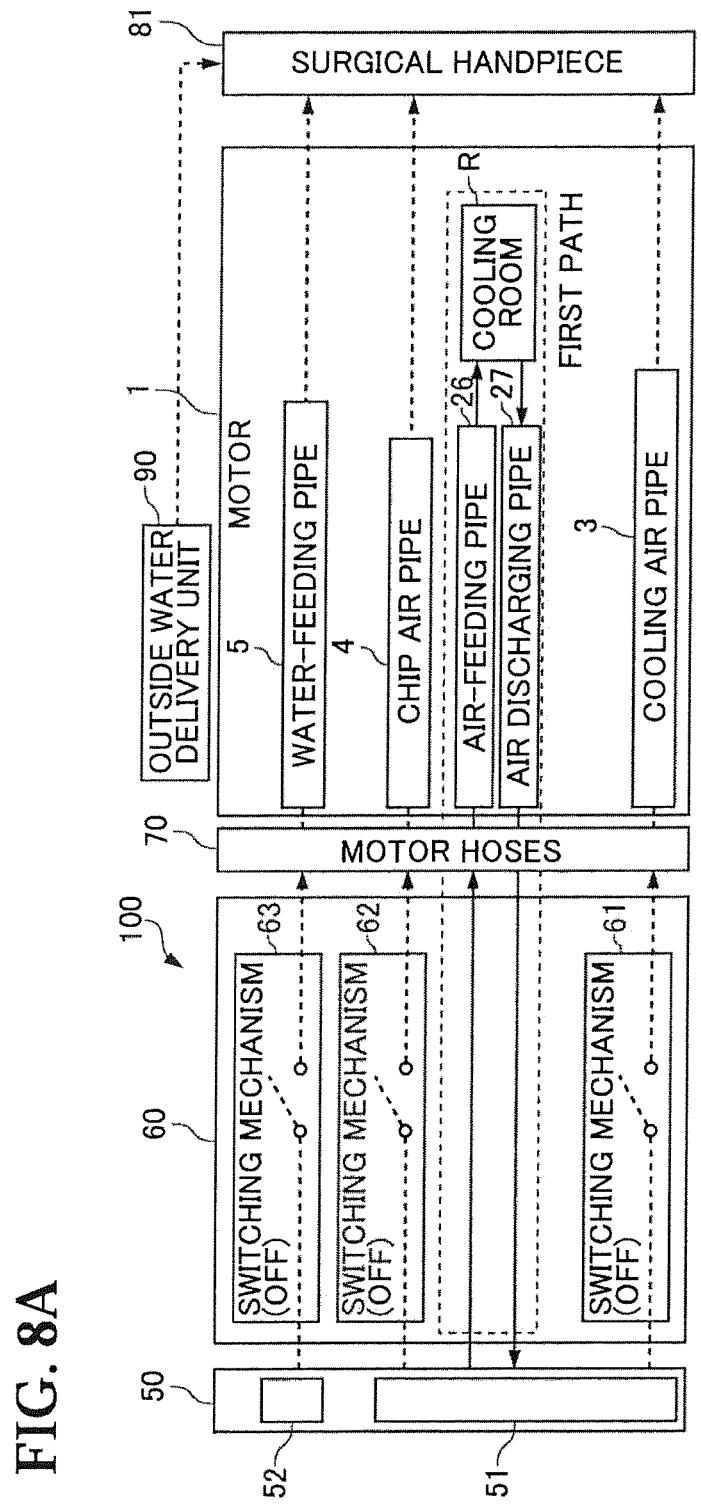
FIG. 8A is the block diagram of FIG. 7 showing when functioned as a surgical handpiece.
Figure 8B:
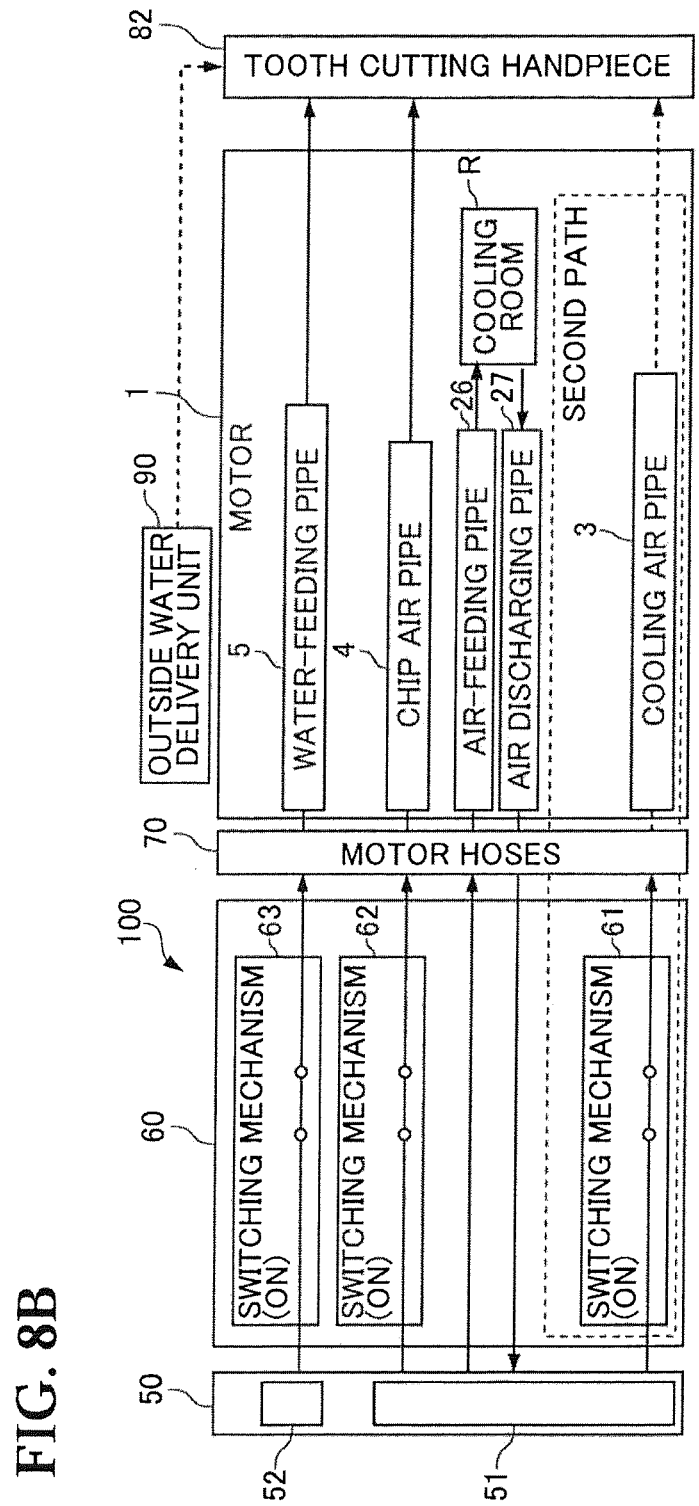
FIG. 8B is the block diagram of FIG. 7 showing when functioned as a tooth cutting handpiece.
Figure 9:
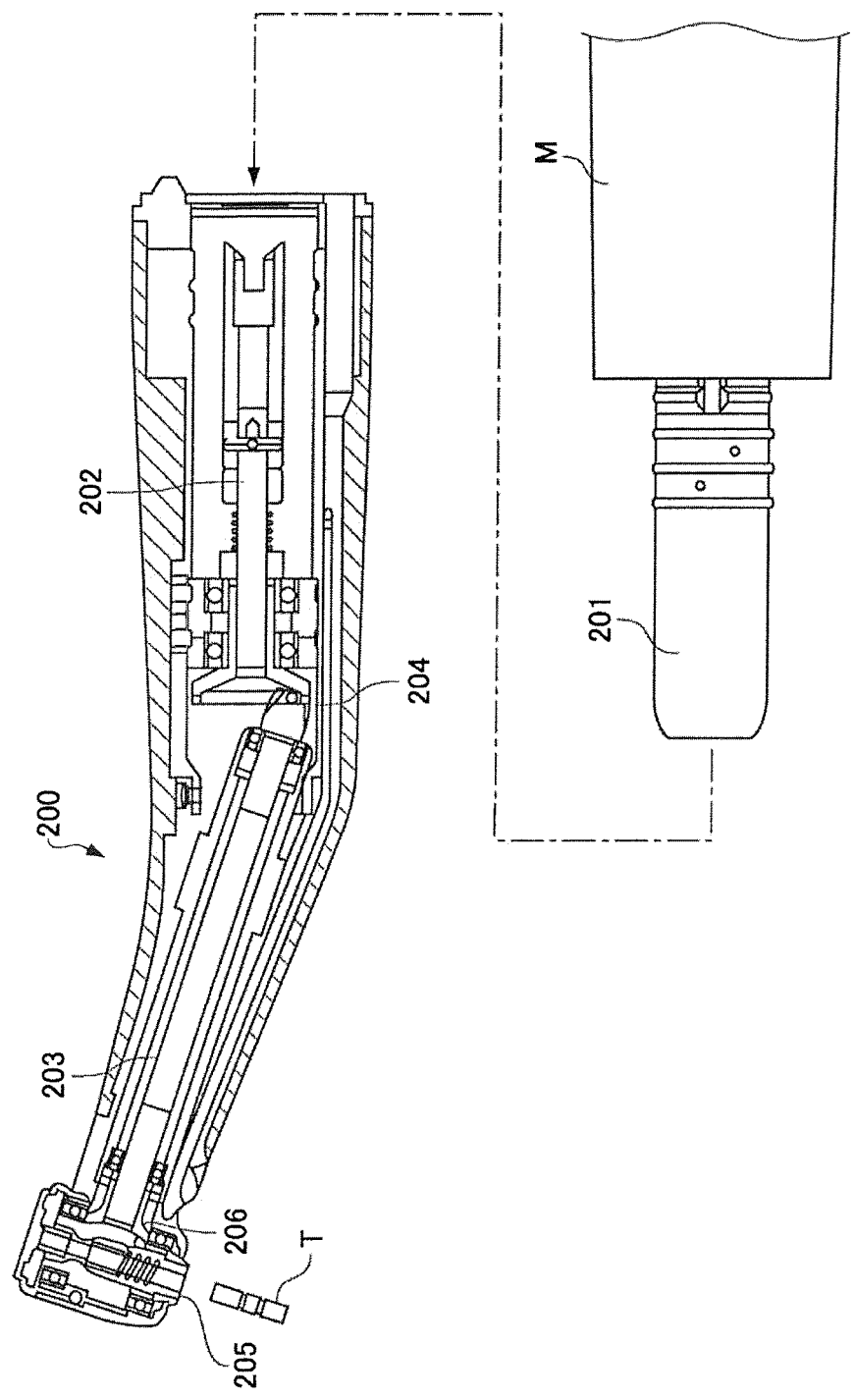
FIG. 9 is a drawing showing the general configuration of a conventional handpiece.

The dental treatment system 100 is able to make use of both surgical treatment in which the surgical handpiece 81 is used by being connected to the motor 1 (FIG. 8A) and general tooth cutting treatment in which the tooth cutting handpiece 82 is used by being connected to the motor 1 (FIG. 8B). In the case of the surgical treatment, the three switching mechanisms 61, 62, 63 are all rendered to be OFF, as illustrated in FIG. 8A. Accordingly, cooling air is supplied from the dental unit 50 to the motor 1 only through the first path (air-feeding pipe 26). Additionally, water is supplied from the outside water delivery unit 90 to the surgical handpiece 81.

On the other hand, in the case of the general tooth cutting treatment, the three switching mechanisms 61, 62, 63 are all rendered to be ON, as illustrated in FIG. 8B. Accordingly, cooling air is supplied from the dental unit 50 to the motor 1 through the second path (cooling air pipe 3) and the chip air pipe 4 in addition to the first path (air-feeding pipe 26). Additionally, water is supplied from the dental unit 50 to the tooth cutting handpiece 82 through the water-feeding pipe 5.

As described above, since the motor 1 comprises the cooling room R (first path), which is isolated from other parts and through which the supplied cooling air is fed around the stator unit 20, it is possible to cool the motor 1 at the occasion of surgical treatment. The thermal capacity of the motor 1 is therefore allowed to be small and downsizing thereof becomes possible. Moreover, the motor 1 is also provided the second path including the cooling air pipe 3 in addition to the first path. As the result, according to the present embodiment, it is possible to cool the rotation transmitting mechanism while cooling the motor 1 at the occasion of the general tooth cutting treatment.

Incidentally, in the above embodiment, the explanation has been given on the precondition that the motor 1 comprises both the first path and the second path, and is used for both a surgical handpiece 81 and a tooth cutting handpiece 82. The present invention is, however, not limited thereto, and in the case of use exclusively for the surgical handpiece 81, the motor 1 is allowed to comprise only the first path. Likewise, in the above embodiment, whether or not to feed cooling air toward the second path and the chip air pipe 4 and also whether or not to feed water toward the water-feeding pipe 5 is controlled by the controller 60, but this is only an example. It is possible to control whether or not to feed the cooling air and whether or not to feed the water by, for example, installing open/close valves in the motor hoses 70 or in the motor 1. Except for those described above, it is possible to choose any configuration from the above embodiment or to modify the configuration of the embodiment without departing from the scope of the present invention.

What is claimed is:

1. A drive motor of a dental handpiece for providing a driving force to a cutting tool of the dental handpiece, the drive motor being connected to the dental handpiece on a front end side of the drive motor, the drive motor comprising:

a cylindrical casing;

a rotor for outputting the driving force, the rotor being rotatably supported inside the cylindrical casing;

a stator provided around the rotor inside the cylindrical casing, wherein the stator comprises:

a stator body including an electromagnetic coil and a magnetic core; and a sleeve holding the stator body; and a first air path through which first cooling air supplied from a rear end side of the drive motor is configured to pass, the first air path comprising an airtight cooling room circumferentially extending between the stator and the cylindrical casing, wherein the first cooling air is further configured to be discharged from the rear end side of the drive motor, and wherein the airtight cooling room is partitioned in a radial direction of the cylindrical casing by the sleeve of the stator.

2. The drive motor of a dental handpiece as recited in claim 1, further comprising a second air path through which second cooling air supplied from the rear end side of the drive motor is configured to pass to be discharged from the front end side of the drive motor.

3. The drive motor of a dental handpiece as recited in claim 2, wherein the first air path and the second air path are independent of each other.

4. The drive motor of a dental handpiece as recited in claim 1, wherein the drive motor is sealed between the cylindrical casing and the stator on both the front end side of the drive motor and the rear end side of the drive motor.

5. A drive motor of a dental handpiece for providing a driving force to a cutting tool of the dental handpiece, the drive motor being connected to the dental handpiece on a front end side of the drive motor, the drive motor comprising:
 a cylindrical casing;
 a rotor for outputting the driving force, the rotor being rotatably supported inside the cylindrical casing;
 a stator provided around the rotor inside the cylindrical casing;
 a first air path through which first cooling air supplied from a rear end side of the drive motor is configured to pass, the first air path comprising an airtight cooling room circumferentially extending between the stator and the cylindrical casing, wherein the first cooling air is further configured to be discharged from the rear end side of the drive motor; and
 a second air path through which second cooling air supplied from the rear end side of the drive motor is configured to pass to be discharged from the front end side of the drive motor,
 wherein a first dental handpiece not having a channel for feeding the second cooling air or a second dental handpiece having a channel for feeding the second cooling air is selectively connected to the front end side of the drive motor;
 wherein when the first dental handpiece is connected, only the first cooling air is fed to the first air path; and
 wherein when the second dental handpiece is connected, the first cooling air is fed to the first air path and the second cooling air is fed to the second air path.

6. A drive motor of a dental handpiece for providing a driving force to a cutting tool of the dental handpiece, the drive motor being connected to the dental handpiece on a front end side of the drive motor, the drive motor comprising:
 a cylindrical casing;
 a rotor for outputting the driving force, the rotor being rotatably supported inside the cylindrical casing;
 a stator provided around the rotor inside the cylindrical casing;
 a first air path through which first cooling air supplied from a rear end side of the drive motor is configured to pass, the first air path comprising an airtight cooling room circumferentially extending between the stator and the cylindrical casing, wherein the first cooling air is further configured to be discharged from the rear end side of the drive motor;
 a second air path through which second cooling air supplied from the rear end side of the drive motor is configured to pass to be discharged from the front end side of the drive motor; and
 a controller configured to control whether to feed the second cooling air to the second air path.

7. The drive motor of a dental handpiece as recited in claim 6, wherein the controller is configured to selectively switch a switching mechanism to control whether to feed the second cooling air to the second air path.

* * * * *